_(12)_ United States Patent  
Rizzotte et al.

(10) Patent No.: US 7,988,912 B2  
(45) Date of Patent: Aug. 2, 2011

(54) ROBOTIC GRIP AND TWIST ASSEMBLY

(75) Inventors: Samuel H. Rizzotte, Fishers, IN (US); Paul N. Avgerinos, Indianapolis, IN (US); Donald A. Turner, Lebanon, IN (US)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 12/574,659

(22) Filed: Oct. 6, 2009

(65) Prior Publication Data

US 2010/0119413 A1 May 13, 2010

Related U.S. Application Data

(63) Continuation of application No. 11/434,048, filed on May 15, 2006, now abandoned.

(60) Provisional application No. 60/682,294, filed on May 18, 2005.

(51) Int. Cl.
*G01N 21/00* (2006.01)
*G01N 31/00* (2006.01)
*G01N 33/00* (2006.01)
*G01N 35/00* (2006.01)

(52) U.S. Cl. ............. 422/63; 422/64; 422/65; 422/500; 901/16; 901/17; 901/18

(58) Field of Classification Search .......... None
See application file for complete search history.

(56) References Cited

U.S. PATENT DOCUMENTS

| | | | |
|---|---|---|---|
| 4,428,710 A * | 1/1984 | Grisebach et al. | ............ 414/590 |
| 5,080,415 A | 1/1992 | Bjornson | |
| 6,264,419 B1 | 7/2001 | Schinzel | |
| 2001/0046437 A1 | 11/2001 | Bramwell et al. | |
| 2003/0114961 A1 | 6/2003 | Riff et al. | |
| 2004/0086368 A1 | 5/2004 | Downs et al. | |
| 2005/0158212 A1 | 7/2005 | Yavilevich | |

FOREIGN PATENT DOCUMENTS

EP 355866 2/1990

* cited by examiner

*Primary Examiner* — Jill Warden
*Assistant Examiner* — Neil Turk
(74) *Attorney, Agent, or Firm* — Merchant & Gould P.C.

(57) ABSTRACT

A microtiter plate transport device is configured to grip a microtiter plate in a first location. The microtiter plate transport device is configured to make a vertical approach to the microtiter plate and grip the microtiter plate in either a portrait orientation or a landscape orientation along either the opposing longer sides or the opposing shorter sides of the microtiter plate. The device comprises a Cartesian coordinate robot including a first gripping member and a second gripping member opposed to the first gripping member. The first gripping member and the second gripping member are supported by an arm configured to move along a vertical axis which extends between the first gripping member and the second gripping member. The first gripping member and the second gripping member are configured to rotate about the vertical axis.

10 Claims, 14 Drawing Sheets

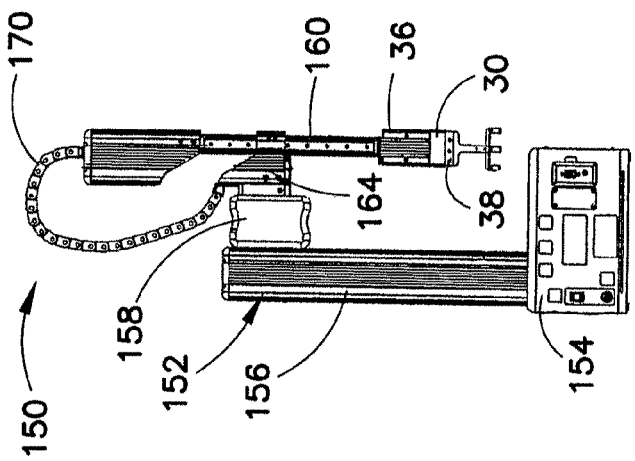
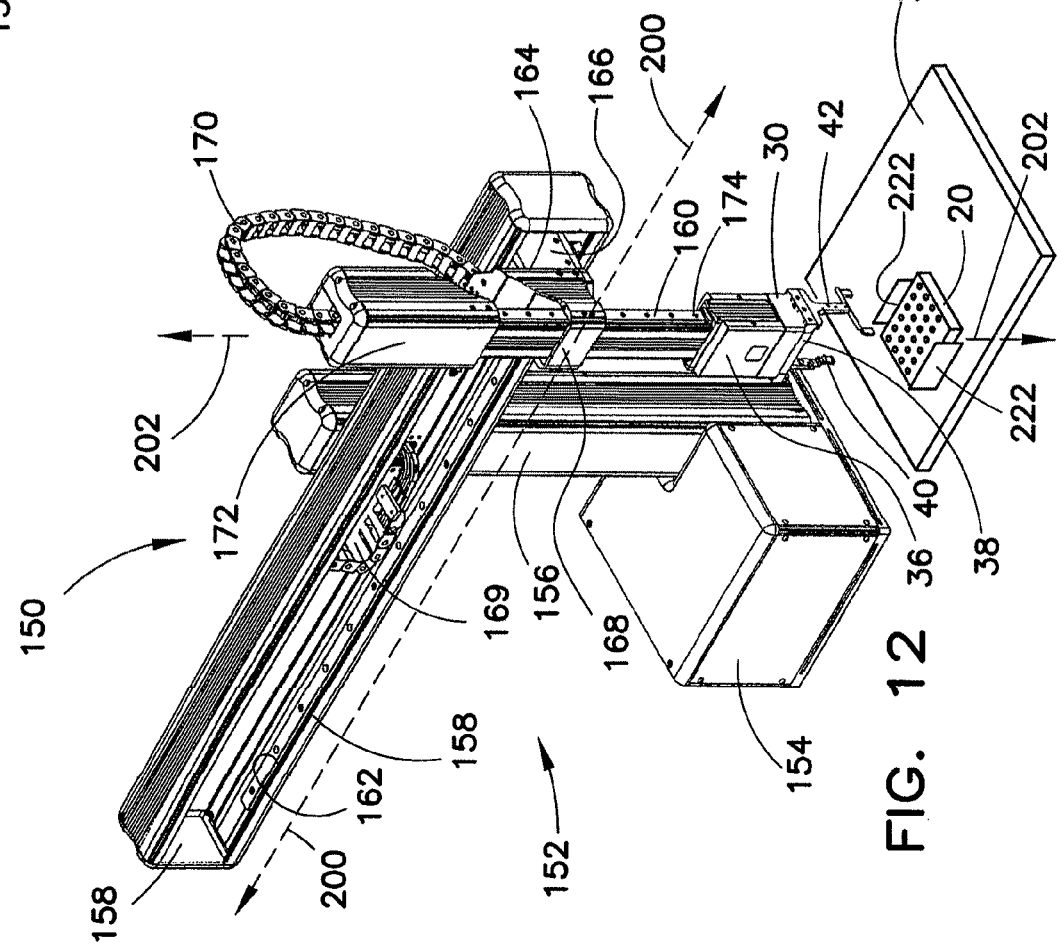

ROBOTIC GRIP AND TWIST ASSEMBLY

CROSS-REFERENCE TO RELATED APPLICATIONS

This application is a continuation of U.S. patent application Ser. No. 11/434,048 filed May 15, 2006, which claims priority from U.S. Patent Provisional Application Ser. No. 60/682,294 filed May 18, 2005, the disclosures of which are incorporated herein by reference in their entirety.

FIELD

The invention relates to the field of laboratory instrumentation, and particularly to robotic grippers for handling laboratory microtiter plates.

BACKGROUND

Microtiter plates (sometimes referred to as "microplates") are plates with multiple individual wells that are commonly used as small test tubes during the experimental process. Microtiter plates typically have 6, 24, 96, 384, or even 1536 sample wells arranged in a 2×3 rectangular matrix. Each well of a microtiter plate typically holds somewhere between a few to a few hundred microliters of liquid.

Robotic mechanisms are often used in the laboratory to transport microtiter plates from one location to another during an experimental assay. For example, a robotic mechanism may be used to transport a microtiter plate from a first station where liquids are dispensed into the wells of the microtiter plate to a second station where the contents of the wells are tested for various characteristics.

Laboratory microtiter plates and the automated laboratory instruments used to handle such microtiter plates are commonly viewed as essential tools in drug discovery research. Because of the need for interaction between microtiter plates and various automated laboratory instruments, dimensional standards have been established for microtiter plates. The makers of automated laboratory instruments have come to rely on these dimensional standards for their products that handle microtiter plates.

The most widely accepted dimensional standards for laboratory microtiter plates have been established by the American National Standards Institute (ANSI) in cooperation with the Society for Biomolecular Screening (SBS). These standards are set forth in ANSI publications ANSI/SBS 1-2004 through ANSI/SBS4-2004. As used herein, the term "standard microtiter plate" is intended to refer to a microtiter plate substantially conforming to these ANSI dimensional standards.

A standard microtiter plate according to ANSI/SBS 1-2004 is shown in FIG. 1. The microtiter plate 20 includes ninety-six wells 21 formed in a rectangular 2×3 matrix. The microtiter plate of FIG. 1 is shown in a landscape orientation with 12 columns and 8 rows. If the microtiter plate of FIG. 1 is rotated 90°, it will be in a portrait orientation with 8 columns and 12 rows of wells. The microtiter plate includes two opposing longer sides 22, 24, with each longer side about 5" in length. The microtiter plate also includes two opposing shorter sides 26, 28, with each shorter side about 3⅜" in length.

During a particular experimental assay, a microtiter plate may need to be oriented in various directions at various times to accommodate various instruments. For example, consider an experimental process where a clean microtiter plate is initially oriented in landscape fashion on a platform. The microtiter plate is then moved to a first instrument where it must be loaded in a portrait orientation. After the microtiter plate is processed by the first instrument, it must be moved to a second instrument which requires loading in a landscape orientation. Following processing by the second instrument, the microtiter plate is unloaded to a cleaning station that requires a portrait orientation. Accordingly, it can be seen that various orientation changes in the microtiter plate may be necessary during a given experimental assay.

Various automated laboratory instruments are available to transport microtiter plates between different locations and different orientations. A common laboratory instrument used to transport microtiter plates is the Cartesian coordinate robot. Cartesian coordinate robots have at least two principal axes of control that are linear and are at right angles to each other. Thus, a Cartesian coordinate robot may include a robotic hand operable to move along a vertical path of travel or a horizontal path of travel. One common type of Cartesian coordinate robot available for transporting microplates is the Gantry robot. Gantry robots generally include a horizontal member supported at a central location or at opposite ends. A carriage is configured to travel upon the horizontal member in a horizontal direction of travel. The carriage is also configured to support a robotic arm configured to move in a vertical direction of travel with respect to the carriage.

Cartesian coordinate robots used to transport microtiter plates are often equipped with opposing grip members configured to rotate with respect to the robotic arm. The opposing grip members are designed to move toward and away from each other by a given stroke distance. When the grip members in a far apart position, they can be moved to the sides of the microtiter plate. When the grip members are then moved to a closer position, the surfaces of the grip members contact opposing sides of the microtiter plate. As the grip members contact the sides of the microtiter plate, a force is applied to the sides of the microtiter plate, and the grip members may be used to pick up and move the microtiter plate from one place to another. Also, the grip members may be rotated with respect to the robotic arm to change the orientation of the microtiter plate from a landscape orientation to a portrait orientation, or vice-versa.

Even though the grip members on the Cartesian coordinate robots described above may be rotated, the robots occasionally encounter problems grasping a microtiter plate. In one situation, a platform holding a microtiter plate may only expose two of the four sides of the microtiter plate to the grip members of the robot. For example, a particular loading platform may expose the shorter sides of the microtiter plate, but may include a wall around the longer sides of the microtiter plate. Such a wall around the longer sides of the microtiter plate will prevent the robot from grasping the microtiter plate if the grip members are designed to grasp the longer sides of the microtiter plate rather than the short sides. Accordingly, it would be advantageous to provide a laboratory robot having opposing grip members operable to move over a sufficient stroke distance in order to allow the grip members to contact either the longer sides or the shorter sides of a standard microtiter plate.

Another situation where laboratory robots sometimes encounter problems in grasping microtiter plates is when there is a significant amount of equipment next to the loading platform. In these situations, the arrangement of the robot and the instruments surrounding the loading platform may prevent the robot from approaching the platform from various horizontal directions. Thus, it would be advantageous to provide a laboratory robot capable of approaching a microtiter plate from a vertical direction. It would be of further advantage if the vertical approach of the robot could occur within a relatively narrow cylindrical column directly above the microtiter plate. In addition, it would be advantageous if such robot comprised opposing grip members configured to rotate about an axis within such relatively narrow cylindrical column.

SUMMARY

A microtiter plate transport device is disclosed herein. The microtiter plate transport device is configured to grip a microtiter plate having a plurality of wells, two opposing first sides and two opposing second sides, wherein the length of each opposing first side is longer than the length of each opposing second side. The microtiter plate transport device is configured to make a vertical approach to the microtiter plate and grip the microtiter plate in either a portrait orientation or a landscape orientation along either the opposing longer sides or the opposing shorter sides of the microtiter plate.

The microtiter plate transport device comprises a Cartesian coordinate robot including a first gripping member and a second gripping member opposed to the first gripping member. The first gripping member and the second gripping member are supported by an arm configured to move in a direction parallel to a vertical axis. The vertical axis is positioned between the first gripping member and the second gripping member, and the first gripping member and the second gripping member are configured to rotate about the vertical axis.

The first gripping member and second gripping member are configured to move relative to each other between a first gripping position and a second gripping position. In the first gripping position, the first gripping member and the second gripping member are adapted to grip the two opposing first sides of the microtiter plate. In the second gripping position, the first gripping member and the second gripping member are configured to grip the two opposing second sides of the microtiter plate.

The arm is supported by a carriage configured to ride on a horizontal track. The carriage is configured to move in a horizontal direction upon the horizontal track. Accordingly the arm and the first and second gripping members are configured to move in both a horizontal and vertical direction. Furthermore, the first and second gripping members are configured to rotate relative to the arm.

With this arrangement, the microtiter plate transport device is configured to grasp a first microtiter plate positioned in a first location in either a portrait or a landscape orientation. The first microtiter plate may then be moved to a second location. During transport, the microtiter plate transport device may rotate the microtiter plate so it is realigned to a new orientation, if required for positioning at the second location. After unloading the first microtiter plate, the grips of the microtiter plate transport device are positioned above a second microtiter plate positioned in the second location. The grip members are then moved vertically downward alongside the second microtiter plate. The grip members are then used to grasp a second microtiter plate at the second location, regardless of the orientation of the second plate. In addition, the second microtiter plate may be grasped along either its longer sides or its shorter sides.

These and other features and embodiments of the microtiter plate transport device will be further understood with reference to the following description and figures. However, the spirit and scope of the appended claims should not be limited to the embodiments described herein.

BRIEF DESCRIPTION OF THE DRAWINGS

FIG. 4A shows a perspective view of the assembled gripper block and lower main housing of FIG. 4;

FIG. 4B shows a side view of the assembled gripper block and lower main housing of FIG. 4;

FIG. 5A shows a perspective view of the assembled robotic grip and twist assembly of FIG. 5;

FIG. 12 shows a perspective view of the robotic grip and twist assembly of FIG. 2 attached to a Cartesian coordinate robot;

FIG. 13 shows a side view of the Cartesian coordinate robot of FIG. 12;

DESCRIPTION

Figure 1:
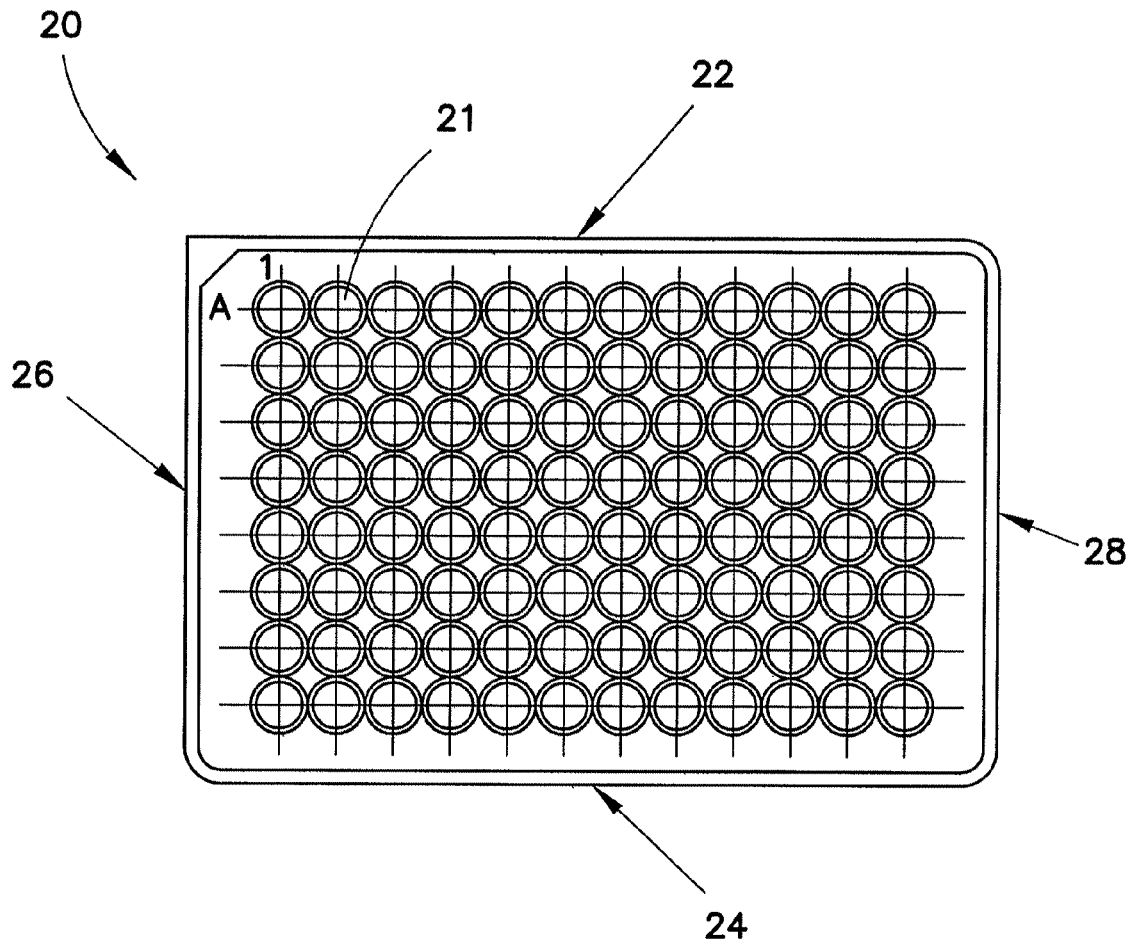
FIG. 1 shows a top view of a ninety-six well microtiter plate.
Figure 2:
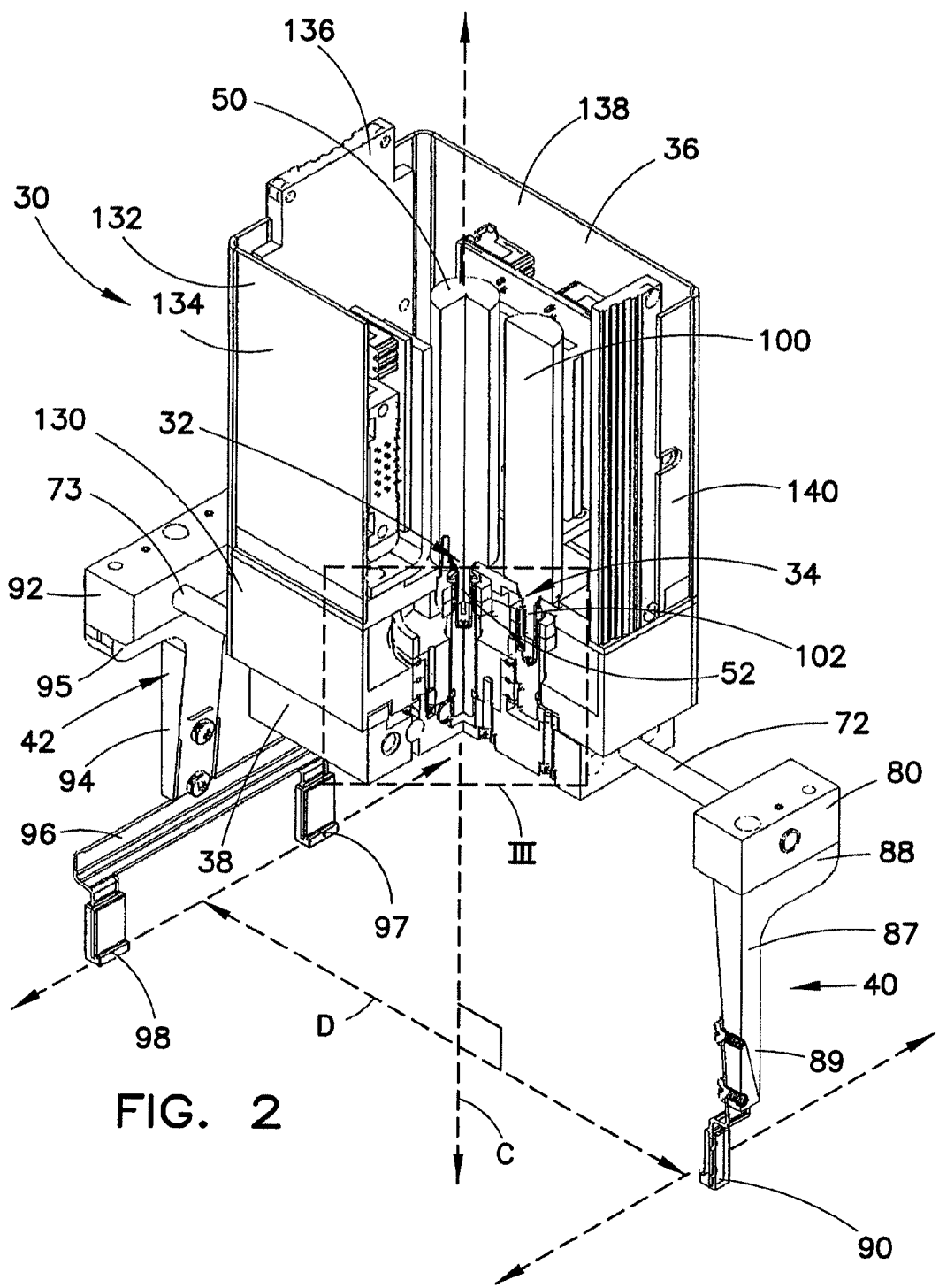
FIG. 2 shows a perspective cutaway view of a robotic grip and twist assembly.

A robotic grip and twist assembly is shown with reference to FIG. 2. The robotic grip and twist assembly 30 is configured for use with a Cartesian coordinate robot. A partial cut-away view of the robotic grip and twist assembly 30 is shown in FIG. 2, with the forward quadrant of the assembly removed to show the interior of the assembly.

As shown in FIG. 2, the robotic grip and twist assembly 30 generally comprises a grip drive 32, a twist drive 34, a main housing 36, a gripper block 38, a first gripping member 40 and a second gripping member 42. The grip drive 32 is configured to drive the first gripping member 40 either away from or towards the second gripping member 42. The twist drive 34 is configured to rotate the gripper block 38 relative to the main housing 36. The main housing 36 provides a covering for the grip drive 32 and the twist drive 34.

Figure 3:
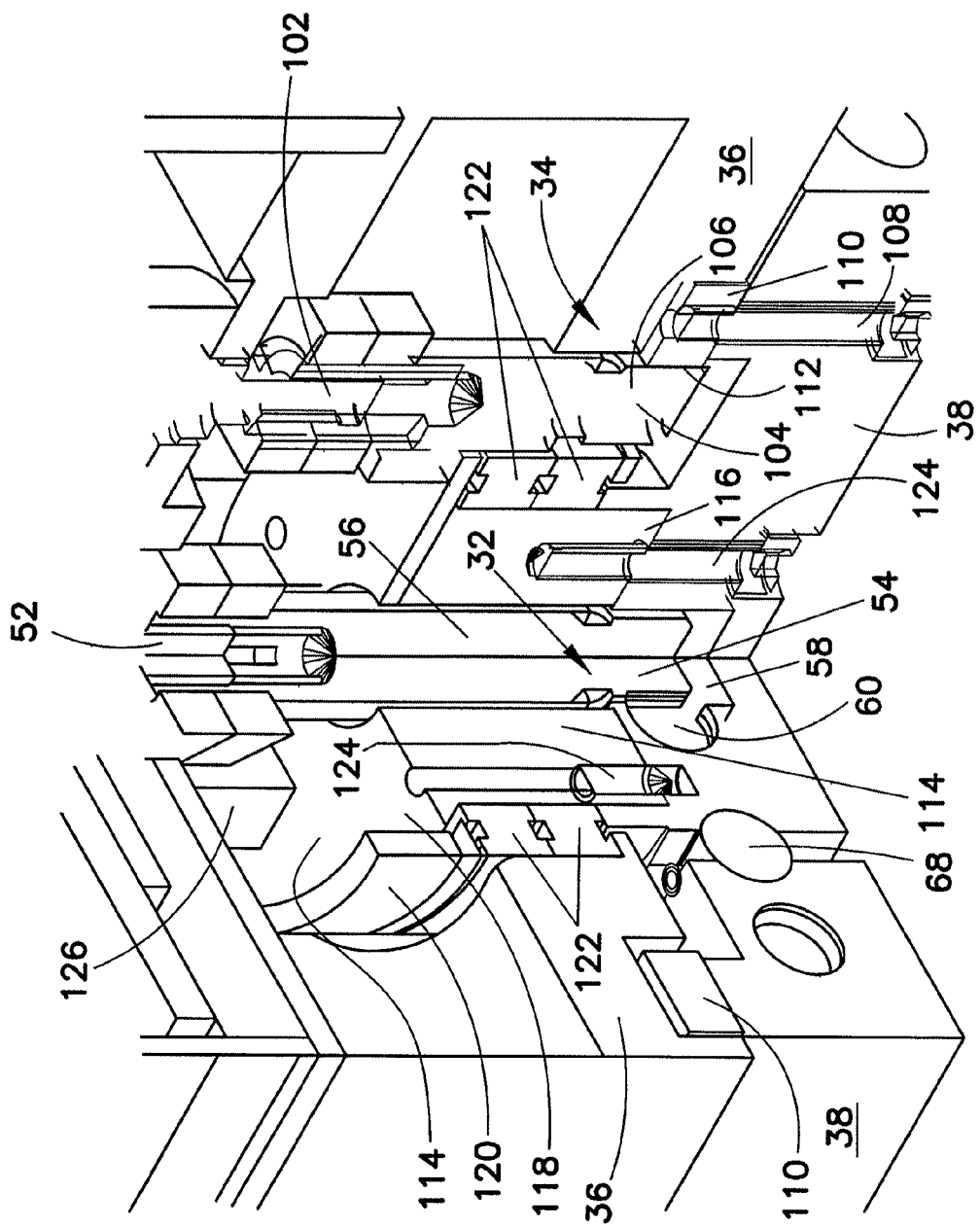
FIG. 3 shows an enlarged view of the portion of FIG. 2 within the dotted lines referenced as box III.
Figure 4:
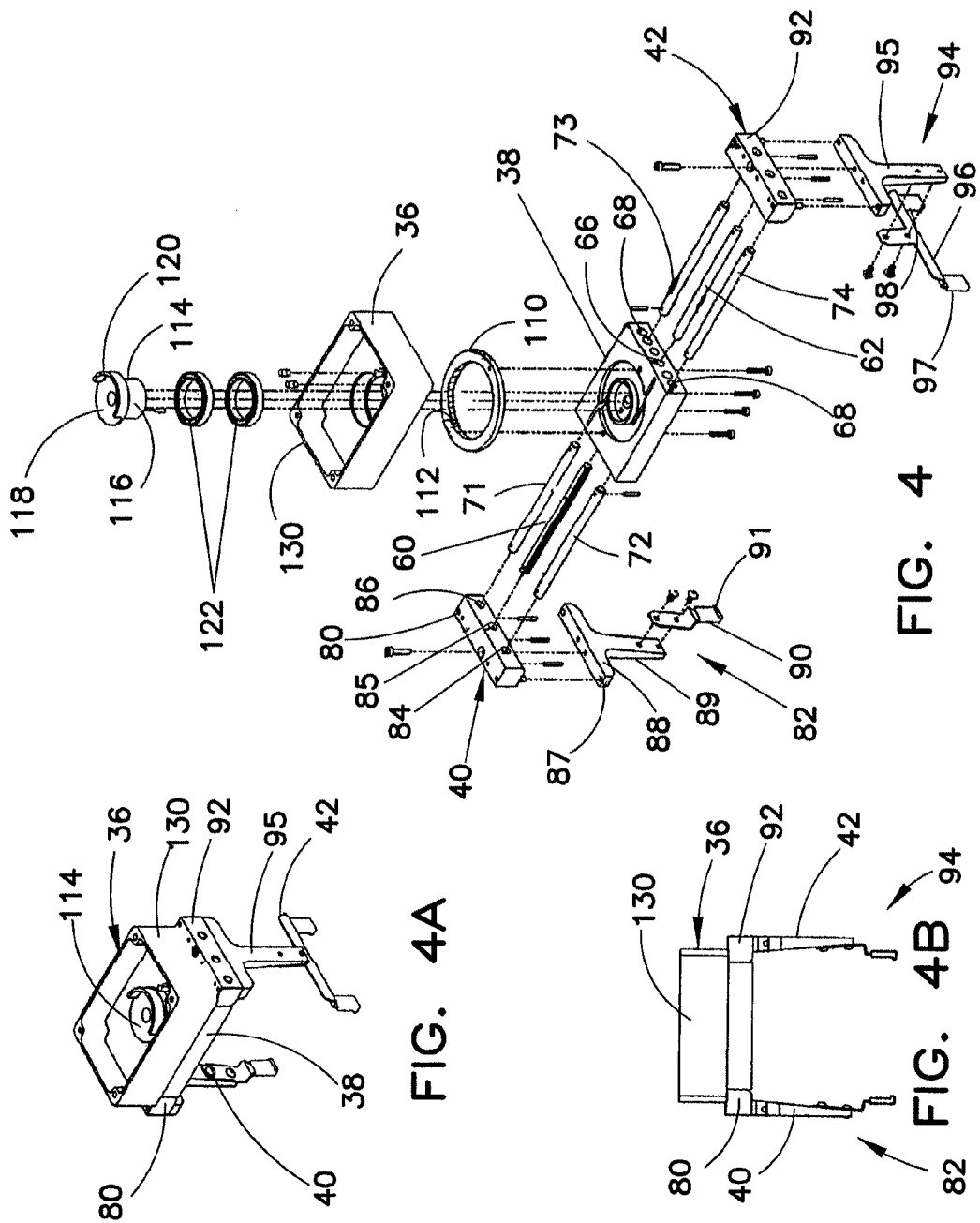
FIG. 4 shows an exploded isometric view of a gripper block and lower main housing of the robotic grip and twist assembly of FIG. 2.

The grip drive 32 includes a grip motor 50 positioned in the center of the main housing 36. The grip motor 50 may be a DC servo-controlled motor having a drive axle 52 extending vertically within the main housing 36. As shown in FIG. 3, a pinion 54 is positioned at the remote end of the drive axle 52. The pinion 54 includes a plurality of pinion teeth 56 configured to engage gear racks 60, 62 retained in the gripper block 38. In particular, as best seen in FIG. 4, the gripper block 38 serves as a grip mount for the first grip member 40 and the second grip member 42, and is configured to retain a first gear rack 60 and a second gear rack 62.

Each gear rack 60, 62 is configured in the shape of a shaft with a plurality of rack teeth 64 extending along one side of the shaft. The gripper block 38 includes elongated cylindrical channels 66 that extend completely through the gripper block and are configured to slideably retain the gear racks 60, 62. The gear racks 60, 62 are oriented in a horizontal direction when retained within the gripper block 38. With the gear racks 60, 62 in this horizontal position, the edges of the rack teeth 64 are oriented in a vertical direction upon the gear racks 60, 62.

As best seen in FIG. 3, the pinion 54 extends into a center hole 58 in the gripper block 38. The gear rack teeth 64 are also exposed to this center hole 58. With this arrangement, the pinion teeth 56 mesh with the teeth 64 of the gear racks 60, 62 during rotation of the pinion.

The first gear rack 60 is located to one side of the pinion 54 and the second gear rack 62 is on an opposite side of the pinion 54, directly opposite the first gear rack 60. Rotation of the pinion 56 results in movement of the first gear rack 60 in one direction and movement of the second gear rack 62 in the opposite direction.

With reference again to FIG. 4, the gripper block 38 is also configured to slideably retain four additional shafts 71-74 within additional channels 68 formed through the gripper mount 38. Two of these shafts are fixed to the first gripping member 40, and two of these shafts are fixed to the second gripping member 42. In particular, shafts 71 and 72 are fixed to the first grip member 40 along with the first gear rack 60. Shafts 73 and 74 are fixed to the second grip member 42 along with the second gear rack 62. Thus, as the pinion drives the first gear rack 60, shafts 71 and 72 slide within channels 68, and the first gripping member 40 moves along with the first gear rack 60 and associated shafts 71, 72. Likewise, as the pinion drives the second gear rack 62, shafts 73 and 74 slide within channels 68, and the second gripping member 42 moves along with the second gear rack 62 and associated shafts 73, 74. As mentioned previously, the pinion 54 drives the first gear rack 60 and the second gear rack 62 in opposite directions, thus the first grip member 40 and the second grip member 42 also move in opposite directions either toward each other or away from each other as the pinion rotates.

The first gripping member 40 comprises a knuckle 80 with a finger 82 extending from the knuckle 80. As best seen in FIG. 4, the knuckle 80 is block shaped and includes three holes 84, 85, 86 in the block. The first hole 84 is configured to fixedly receive shaft 71, the second hole 85 is configured to fixedly receive the gear rack 60, and the third hole is configured to fixedly receive shaft 72. Accordingly, as the gear rack 60 is driven by the pinion 54, the knuckle 80 moves back and forth with the gear rack 60. Likewise, because shafts 71 and 72 are fixed to the knuckle 80, they also slide back and forth with the gear rack 60.

The finger 82 attached to the knuckle 80 includes a T-shaped appendage 87. The upper horizontal portion 88 of the T-shaped appendage 87 is fixed to the knuckle 80. The lower vertical portion 89 of the T-shaped appendage 87 extends downward, away from the knuckle 80. A fingertip 90 is connected to the distal end of the lower vertical portion 88. The fingertip 90 includes a gripping surface 91 designed to contact the sidewalls of a microtiter plate. The gripping surface 91 is typically comprised of a relatively soft resilient rubber or plastic material that resists slipping when the microtiter plate is contacted by the gripping surface 91.

The second gripping member 42 is positioned opposite the first griping member 40 on the gripper block 38. The second gripping member 42 is similar to the first gripping member 40, and includes knuckle 92 fixed to the second gear rack 62 and shafts 73 and 74. A finger 94 extends from the knuckle 92. The finger 94 includes a T-shaped appendage 95 with a cross-bar 96 fixed to the lower end of the T-shaped appendage. A first gripping surface 97 is secured to one end of the cross-bar 96, and a second gripping surface 98 is secured to the other end of the other end of the cross-bar 96. The gripping surfaces 97 and 98 are comprised of a relatively soft resilient rubber or plastic material that resists slipping when the microtiter plate is contacted by the gripping surfaces.

Figure 6:
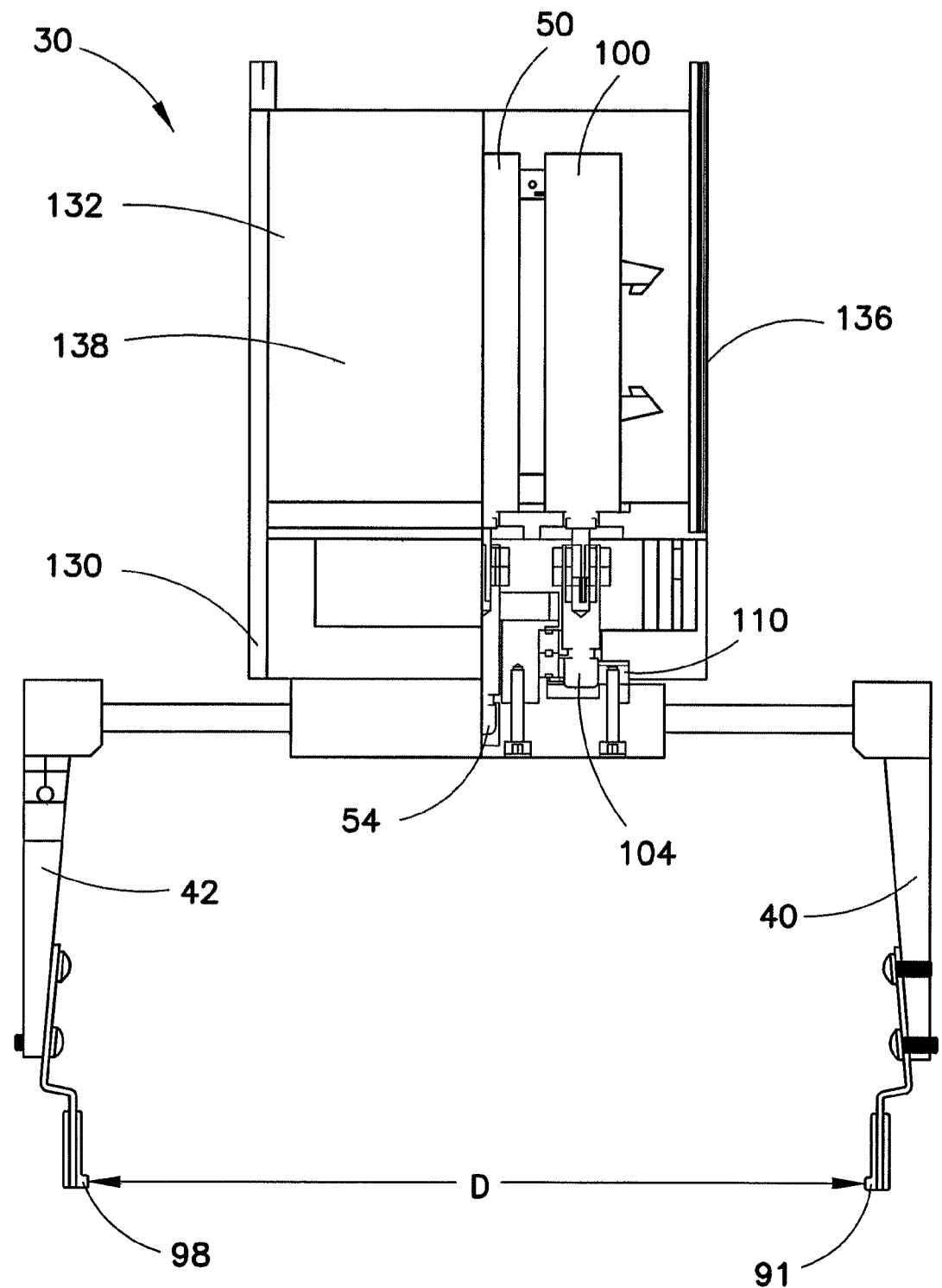
FIG. 6 shows a first side view of the robotic grip and twist assembly of FIG. 2.
Figure 7:
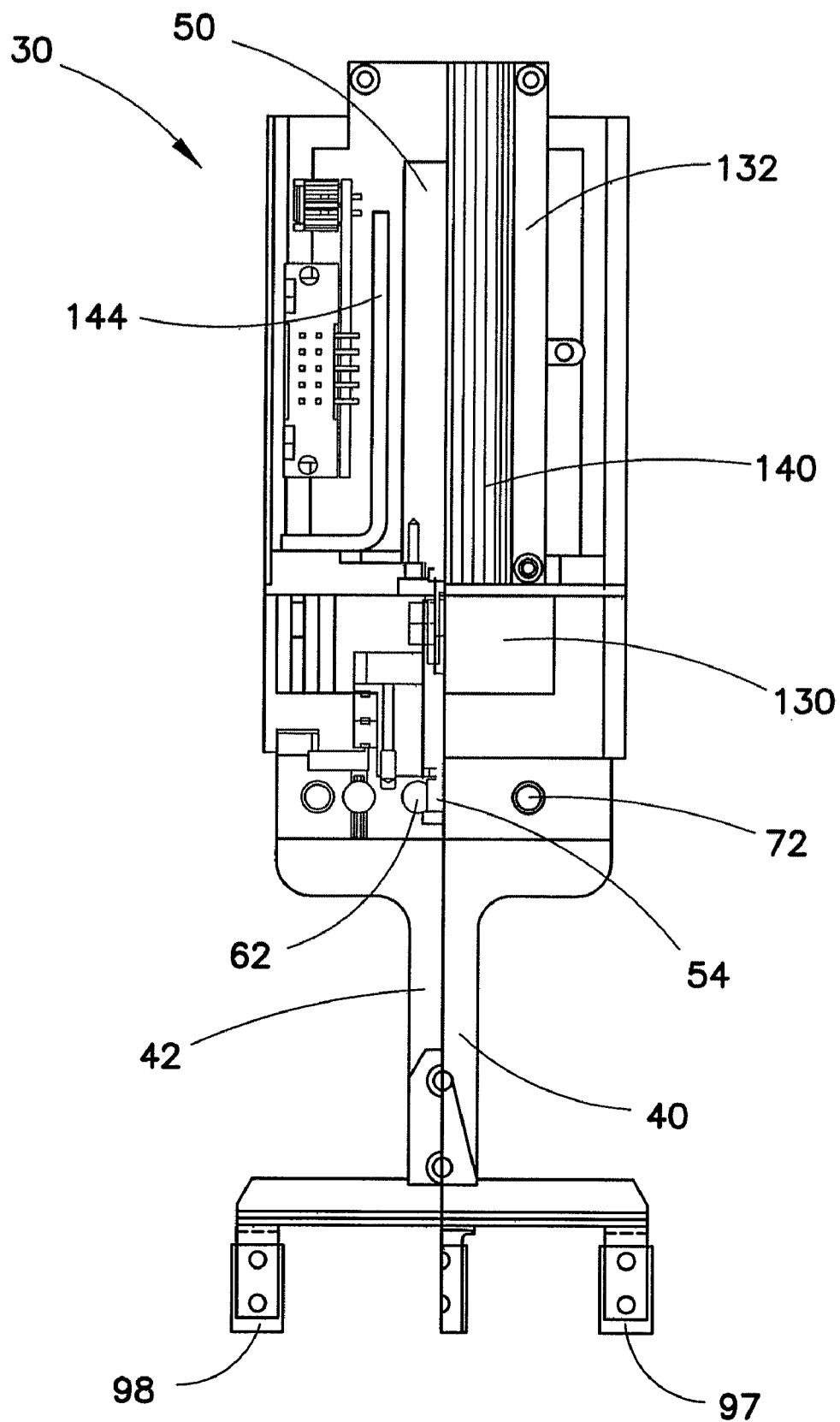
FIG. 7 shows a second side view of the robotic grip and twist assembly of FIG. 2.
Figure 8:
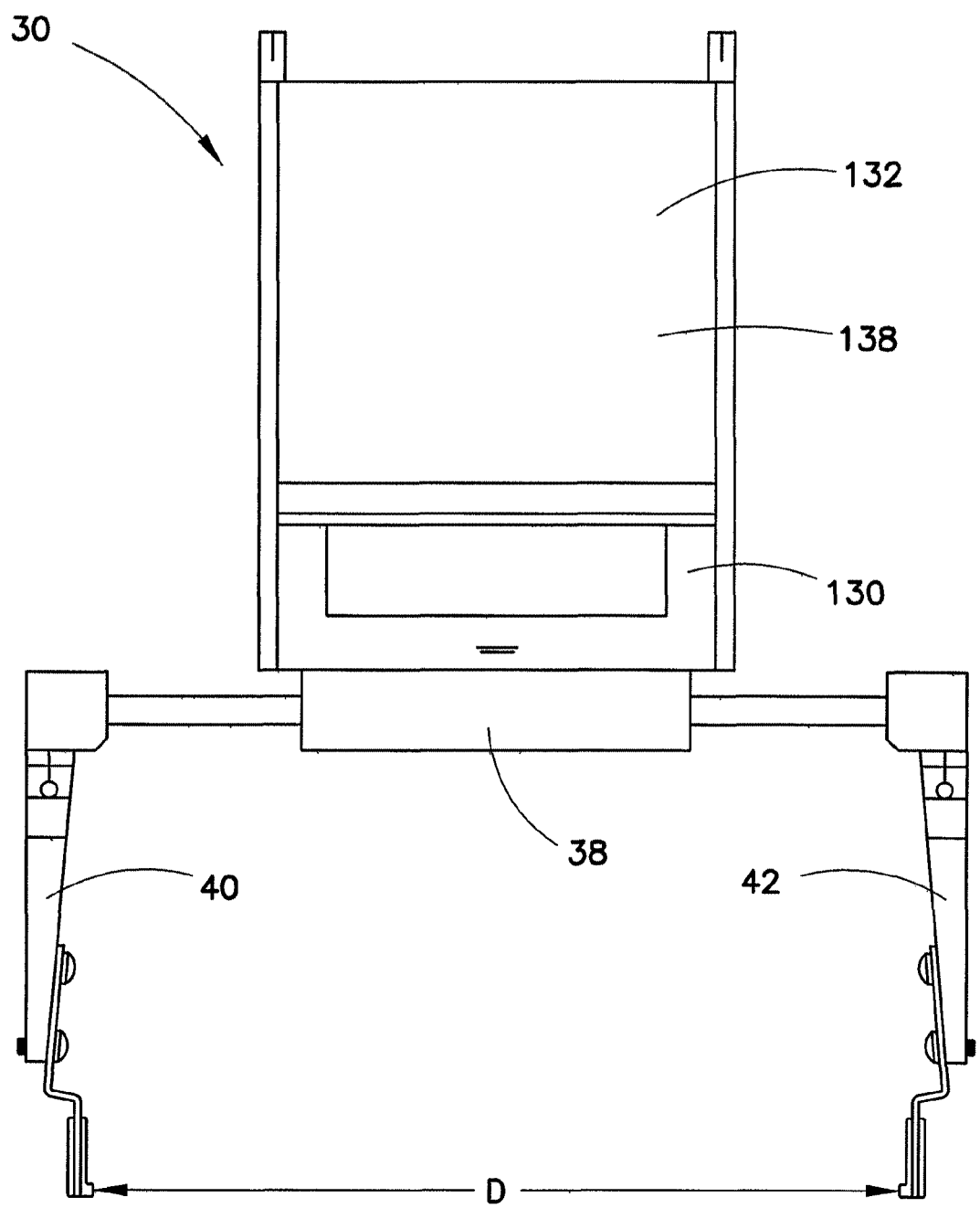
FIG. 8 shows a third side view of the robotic grip and twist assembly of FIG. 2.
Figure 9:
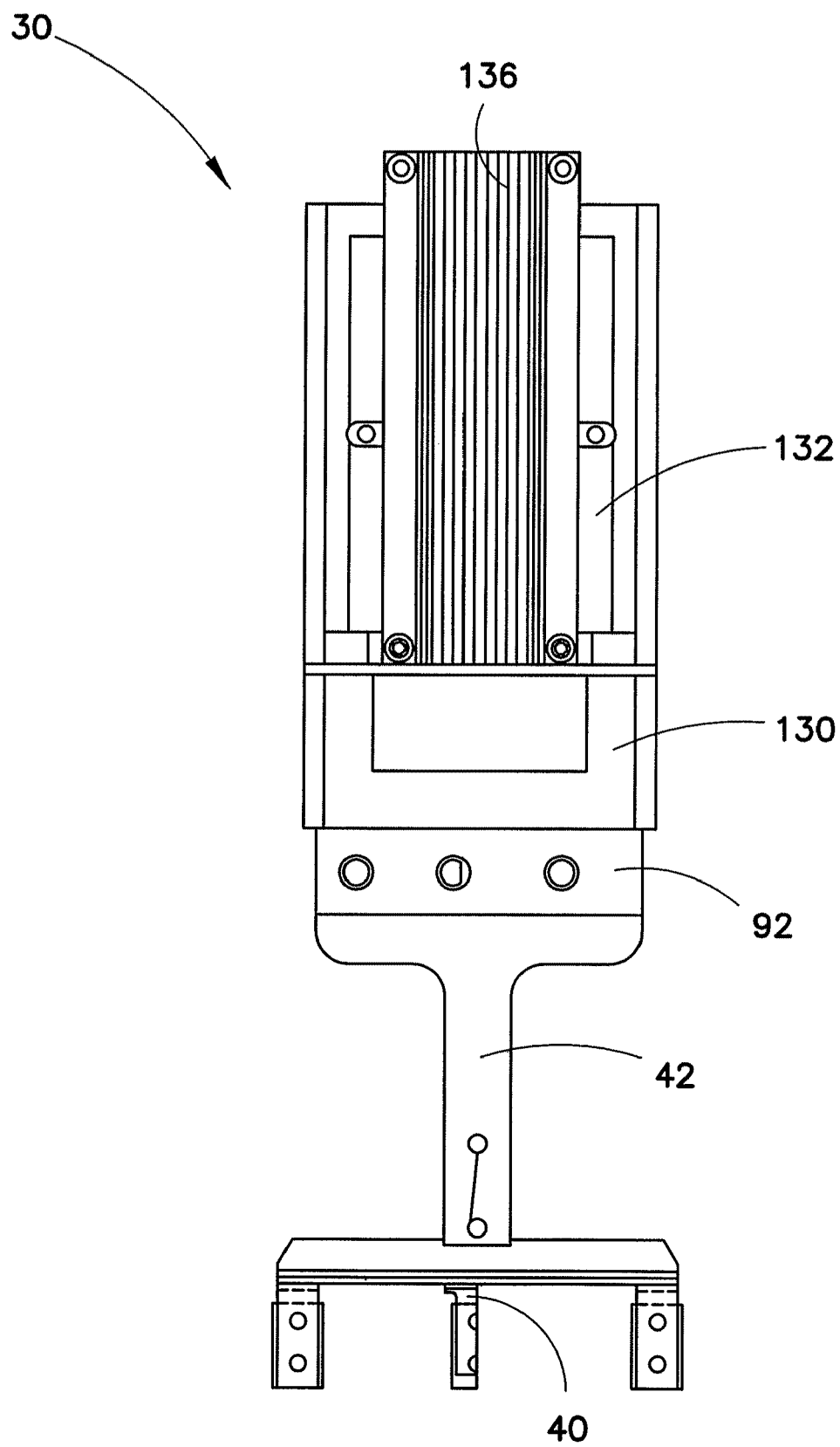
FIG. 9 shows a fourth side view of the robotic grip and twist assembly of FIG. 2.
Figure 10:
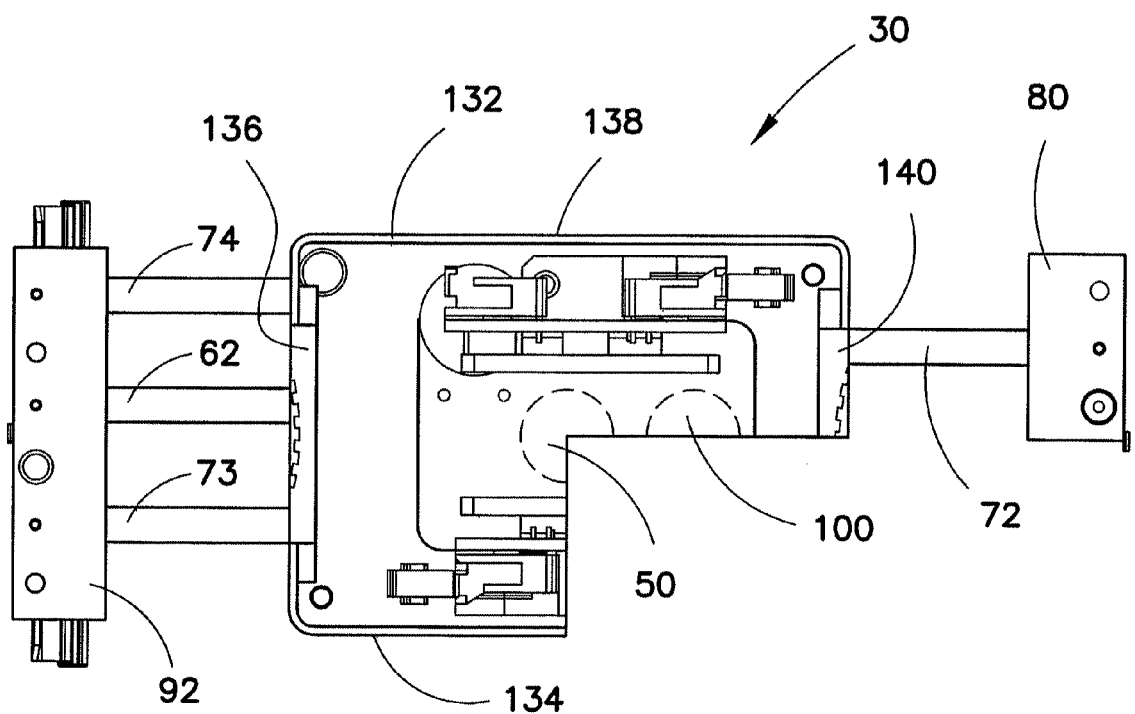
FIG. 10 shows a top view of the robotic grip and twist assembly of FIG. 2.
Figure 11:
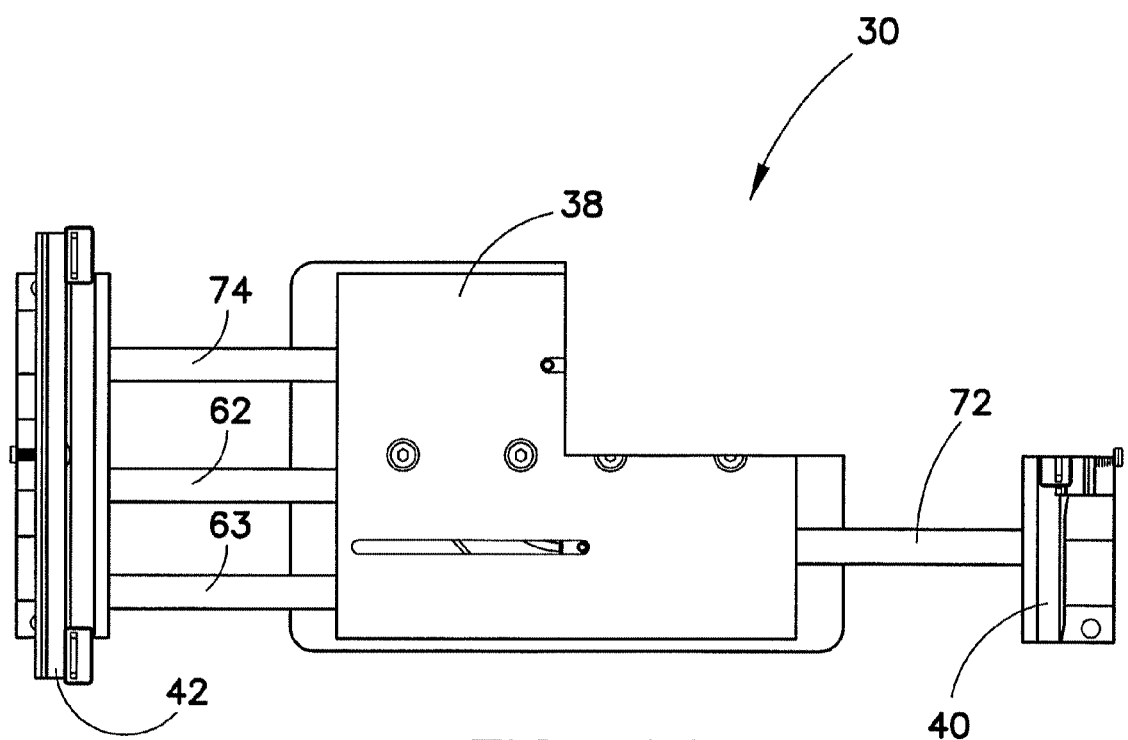
FIG. 11 shows a bottom view of the robotic grip and twist assembly of FIG. 2.

As shown in FIGS. 2, 6 and 8, the first gripping member 40 and the second gripping member 42 are separated by a distance D. The first gripping member 40 and the second gripping member 42 may be driven by the grip motor 50 between a first position where the griping members are closer together and a second position where the gripping members are further apart. In one embodiment, the distance D is equal to 3⅜" or slightly less in the first position. In this first position, the gripping surfaces 91, 97 and 98 are able to contact and grip the longer sides 22 and 24 of a standard microtiter plate. In the second position, the distance D is equal to 5" or slightly more. In this second position, the gripping surfaces 91, 97 and 98 are able to contact and grip the shorter sides 26 and 28 of a standard microtiter plate. The difference between an innermost position and an outermost position of the gripping members 40 and 42 is sometimes referred to as the "stroke" of the gripping members. Thus, in the embodiment disclosed herein, the stroke of the gripping members is greater than 1⅝".

With reference again to FIGS. 2-4, the twist drive 34 includes a twist motor 100 positioned next to the grip motor 50 within the main housing 36. The twist motor 100 may be a DC servo-controlled motor having a drive axle 102 extending vertically within the main housing 36. As shown in FIG. 3, a pinion 104 is positioned at the remote end of the drive axle 102. The pinion 104 includes a plurality of pinion teeth 106 configured to engage a ring gear 110 secured to the gripper block 38. The ring gear 110 is fixed to the gripper block 38 with a plurality of pins 108 that extend between the gripper block 38 and the ring gear 110, locking the ring gear 110 in place relative to the gripper block 38. A plurality of teeth 112 are provided around the interior of the ring gear 110. These teeth 112 are configured to mesh with the teeth of the pinion 104 of the twist drive 34. Therefore, as the pinion rotates, it drives the ring gear 110 in a circular fashion about its center axis (which is coaxial with the drive axle 52 of the grip drive). Because the ring gear 110 is fixed to the gripper block 38, the gripper block 38 also rotates with the ring gear 110.

A bearing lock 114 is also fixed to and rotates with to the gripper block 38. The bearing lock 114 includes a lower cylinder 116 attached to an upper disc 118. A semi-cylindrical flag 120 extends upward from the upper disc 118. Radial bearings 122 separate the main housing 36 from the bearing lock 112. The upper disc 118 portion of the bearing lock 114 rests on the radial bearings 122 while the lower cylinder 116 portion of the bearing lock 114 extends through the radial bearings 122 and contacts the gripper block 38. Pins 124 secure the bearing lock 114 to the gripper block 38. Accordingly, when the gripper block 38 is driven by the twist drive 34 and rotates, the bearing lock 114 also rotates and rotatably supports the gripper block 38 relative to the main housing 36.

A sensor 126 is mounted in the main housing 36 in order to track the position of the gripper block 38 as it rotates. In one embodiment, the sensor 126 may be an optical sensor configured to detect the presence of the flag 120. As the twist motor 100 operates to rotate the gripper block 38 and attached bearing lock 114, the sensor detects the position of the flag 120 on the bearing 122 to confirm that the orientation of the gripper block 38 is as expected.

Figure 5:
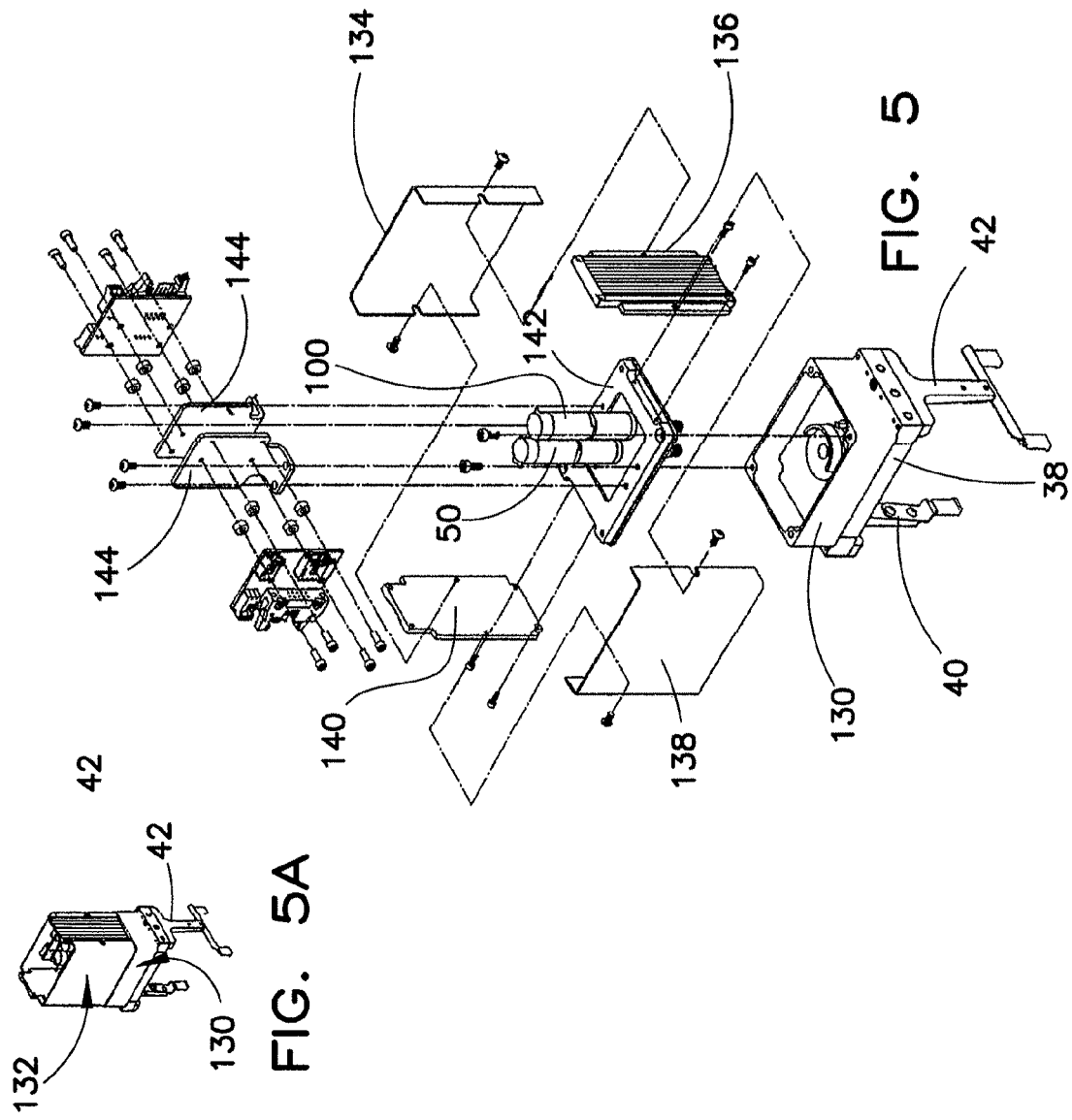
FIG. 5 shows an exploded isometric view of an upper main housing of the robotic grip and twist assembly of FIG. 2.

The grip drive 32 and twist drive 34 are both generally contained within the main housing 36. As best seen in FIG. 5, the main housing comprises a lower box structure 130 and an upper box structure 132. In one embodiment, as shown in FIG. 4, the lower box structure 130 is comprised of a single integral component having four sidewalls configured in a rectangular shape. The four side walls of the lower box structure 130 define an area that is slightly overlaps the footprint of the gripper block 38. However, as best seen in FIGS. 4A and 4B, the knuckles 80 and 92 attached to the gripper block 38 extend outside the area defined by the lower box structure 130.

With general reference to FIGS. 5-11, and particular reference to FIG. 5, the upper box structure 132 includes four side panels 134, 136, 138 and 140 connected by fasteners such as screws or nuts and bolts. An intermediate platform 142 is positioned between the lower box structure 130 and the upper box structure 132. The intermediate platform 142 covers the top of the lower box structure 130 and serves as the floor of the upper box structure 132. The grip motor 50 and the twist motor 100 are both attached to the intermediate platform, with the drive axis of each motor extending through the platform 142 and into the lower box structure 130 and the gripper block 38, where they engage other components of the grip drive 32 and twist drive 34, as discussed above. Additional boards 144 are attached to the intermediate platform 142. These additional boards 144 hold electrical components, connectors, and related support members necessary to operate and provide power to the assembly 30 and generally connect the assembly 30 to other components, such as a robotic arm. Such additional components, connectors and support members required to connect and operate the assembly will be recognized by those of skill in the art. As shown in FIG. 5A, when the panels 134, 136, 138, and 140 are assembled, the grip motor 50, twist motor 100, boards 144 and related components are all contained within the space defined by the panels 134, 136, 138, 140.

FIGS. 12 and 13 show the grip and twist assembly 30 mounted as part of a robotic transport device 150. The robotic transport device is a Cartesian coordinate robot 152. In the embodiment shown in FIG. 12, the Cartesian coordinate robot 152 includes a base 154, a vertical tower 156, a horizontal support 158, and a robotic arm 160. The vertical tower 156 is fixed to the base 154 and provides a mounting platform for the horizontal support 158. The horizontal support 158 includes a track 162. A carriage 164 rides upon the track 162. The horizontal support 158 defines a horizontal liner path of movement 200 for the robot. Drive arrangements configured to move a carriage upon a horizontal track will be known to those of ordinary skill in the art. A flexible connector member 169 is connected between the horizontal support 158 and the carriage 164. The flexible connector member 169 retains conductors configured to deliver electrical power and/or signals between the horizontal support 158 and the carriage 164. These electrical conductors are joined to other electrical conductors and related electrical components housed in the base 154. For example, a microprocessor may be housed in the base 154 which delivers control signals to the carriage 164.

The carriage 164 includes a track member 166 and an arm support member 168. The track member 166 of the carriage 164 engages the track 162 of the horizontal support 158. The arm support member 168 of the carriage 164 is configured to retain the robotic arm 160 in a vertical orientation. The arm support member 168 also defines a vertical linear path of movement 202 for the robot.

The robotic arm 160 is configured to move relative to the carriage 164 in a vertical direction along a vertical linear path of movement 202. To this end, the support member 168 includes a drive train which engages the robotic arm 160 and moves the robotic arm 160 up and down. Robotic arm and drive train arrangements configured to move the robotic arm up and down will be known to those of ordinary skill in the art. Portions of the robotic arm 160 move through the arm support member 168 as the robotic arm is driven in the vertical direction along axis 202.

A flexible connector member 170 is connected to the upper end of the robotic arm 160. The flexible connector member 170 includes conductors which communicate electrical power and/or signals between the carriage 164 and the robotic arm 160. Additional electrical conductors are channeled through the robotic arm 160 to the grip and twist assembly 30, which is positioned at the lower end 174 of the robotic arm. The main housing 36 of the grip and twist assembly 30 is fixed to the robotic arm 160 using any of various fasteners.

In operation, the robotic grip and twist assembly 30 is configured for use with a Cartesian coordinate robot 152, such as that shown in FIG. 12. The Cartesian coordinate robot 152 is adapted to move the robotic grip and twist assembly 30 in a horizontal direction by moving the carriage 164 along the horizontal support 158, thus moving the robotic arm 160 and grip and twist assembly 30 in a horizontal direction. The robot 152 is configured to move the grip and twist assembly 30 in a vertical direction by moving the robotic arm 160 in a vertical direction relative to the carriage 164, thus moving the grip and twist assembly 30 in a vertical direction. Accordingly the robotic grip and twist assembly 30 may be positioned at any location in the area defined by the limits of movement of the assembly 30 along the horizontal linear axis of movement 200 and the vertical linear axis of movement 202.

In addition to horizontal and vertical movements, the grip and twist assembly is configured to twist by rotation of the gripper block 38 relative to the main housing 36. In particular, with reference again to FIGS. 2 and 3, when the twist motor 100 turns the pinion 104 which engages the ring gear 110, the ring gear 110 rotates, causing the grip block 38 to rotate relative to the main housing 36. With this rotating action, the opposing first grip member 40 and second grip member 42 may be oriented in a north/south or east/west type arrangement, or various orientations in between. The rotational movement of the gripper block 38 is represented by arrow 206 in FIG. 14. Arrow 206 shows that rotation of the gripper block 38 causes the gripper block 38 to pivot about vertical axis 202.

Figure 14:
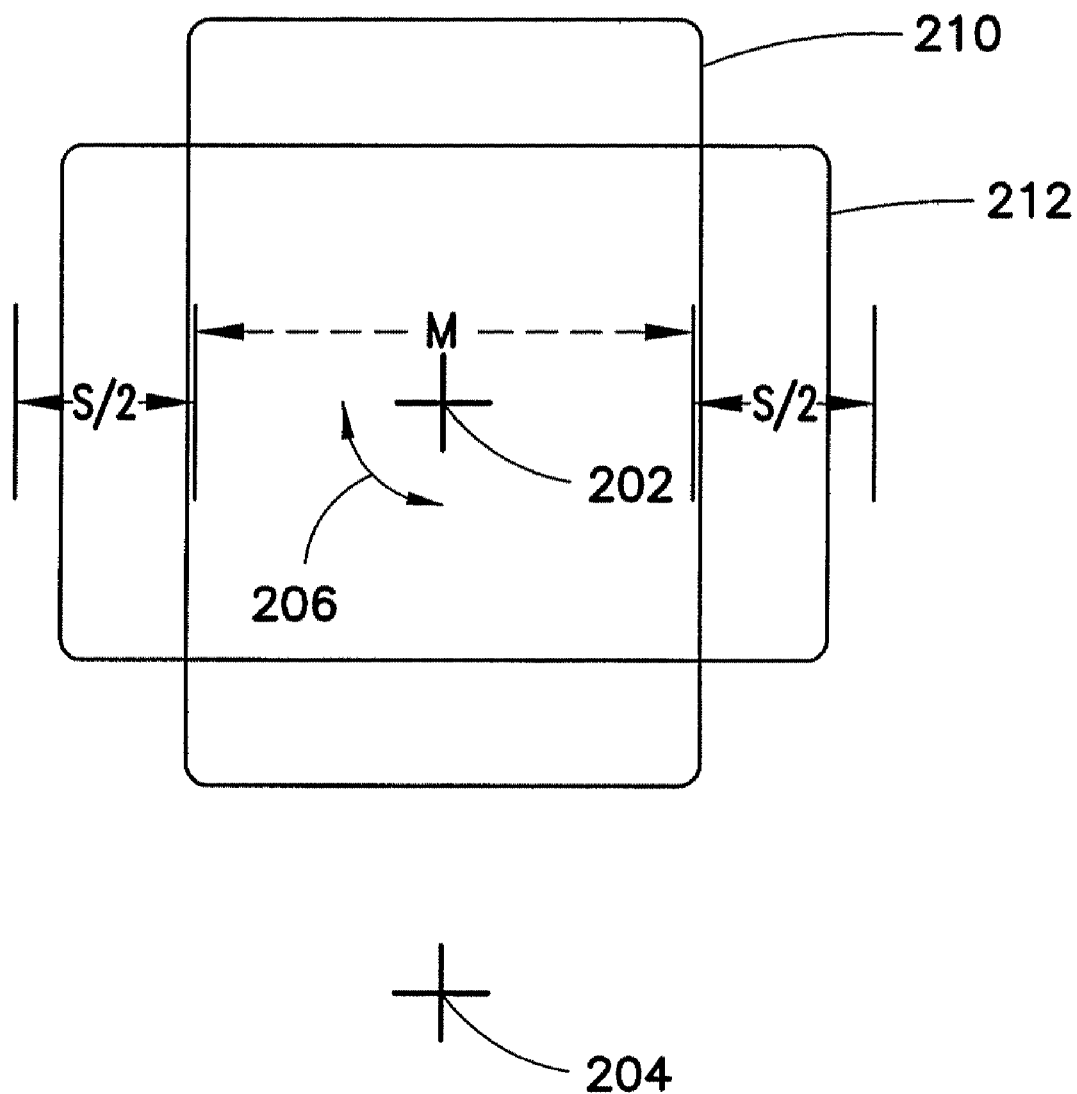
FIG. 14 is a diagram showing the footprint of a microtiter plate when grasped by the robotic grip and twist assembly of FIG. 2 in a portrait orientation and a landscape orientation.

FIG. 14 also shows that the stroke of the grip and twist assembly 30 is such that the first grip member 40 and second grip member 42 may grip a microtiter plate in either a portrait or landscape orientation and on either the shorter or longer sides of the microtiter plate. The microtiter plate footprint shown in FIG. 14 with reference numeral 210 represents a portrait orientation. The microtiter footprint shown with reference numeral 211 represents a landscape orientation. The grip and twist assembly 30 is configured such that the minimum distance M between the first grip member 40 and the second grip member 42 will allow the longer sides of a standard microtiter plate to be grasped. In particular, the minimum distance M shown in FIG. 14 is slightly less than 3⅜", which allows the grip members to contact the longer sides of a standard microtiter plate and apply some amount of force to the sides. In one embodiment, M=3¼".

While the minimum distance between the grip members 40, 42 is M in FIG. 14, the maximum distance between the grip members is M+S, where S is the stroke of the grip members. When the grip members 40, 42 are moved to their maximum distance apart the distance between the grip members, M+S, will be slightly more than 5". In one embodiment, M+S=5¼", and S=2". Because the grip members 40, 42 are allowed to move more than 5" apart, the grip members 40, 42 may be moved alongside the shorter sides of a standard microtiter plate and then moved toward each other such that the grip members 40, 42 contact the shorter sides of the microtiter plate.

As set forth above, the grip and twist assembly 30 described herein is configured for horizontal, vertical, and rotational movement. In addition, the grip and twist assembly has a stroke distance that allows the grip members 40, 42 to grasp a standard microtiter plate along either the shorter sides or the longer sides. As shown in FIG. 12, the grip and twist assembly 30 is configured to make a vertical approach to a microtiter plate 20 along the vertical axis 202. The vertical axis 202 passes through the footprint of the microtiter plate to be grasped, and the grip members 40, 42 may be rotated about this vertical axis. Furthermore, the grip members 40, 42 are configured to move toward and away from the vertical axis 202. The stroke of the grip members 40, 42 is sufficient to move the grip members 40, 42 between a first position where the grip members grasp the longer sides of the microtiter plate, and a second position where the grip members grasp the shorter sides of the microtiter plate.

With continued reference to FIG. 12, a microtiter plate 20 is shown positioned on a loading platform 220. The microtiter plate 20 is situated between to opposing boundary walls 222 which prevent access to the longer sides of the microtiter plate 20. Thus, the microtiter plate 20 must be gripped along its shorter sides if the grip and twist assembly 30 is to grasp and remove the microtiter plate from the platform 220. When transporting the microtiter plate 20, the robotic grip and twist assembly 30 is first moved into position directly over the microtiter plate 20 such that the vertical axis 202 extends through the microtiter plate. The twist motor 100 is then rotated to align the gripper block 38 with the microtiter plate, thus positioning the grip members 40, 42 to grasp the microtiter plate along the shorter sides. Next, the grip motor 50 drives the grip members 40, 42 apart. Specifically, the grip members 40, 42 are moved more than 5" apart so they may be positioned alongside the shorter sides of the microtiter plate 20. The robotic arm 160 is then driven downward until the grip members 40, 42 are positioned alongside the shorter sides of the microtiter plate 20. After this, the grip motor 50 drives the grip members 40, 42 toward each other, causing the grip members 40, 42 to contact the shorter sides of the microtiter plate 20 and apply a predetermined force against the sides of the microtiter plate. With the microtiter plate 20 grasped between the grip members 40, 42, the microtiter plate may be moved to another location by the robotic transport device 150. Furthermore, the orientation of the microtiter plate may be changed by the robotic transport device 150 during the move, if appropriate.

As described above, the grip and twist assembly 30 is configured to grip a standard laboratory microtiter plate in either a portrait or landscape orientation and along either the longer or shorter sides of the microtiter plate. Furthermore, the grip and twist assembly 30 is configured to make a vertical approach to the microtiter plate 20 along a vertical axis that extends through the footprint of the microtiter plate, such as vertical axis 202 of FIG. 12. In FIG. 12, the vertical approach axis is shown as the same axis that the robotic arm 160 moves along. However, in an alternative embodiment, the vertical approach axis need not be the same axis that the robotic arm moves along. For example, if the robotic arm 160 is L-shaped, the vertical approach axis may be removed from the axis that the robotic arm moves along. A representation of this is shown in FIG. 14 with reference to vertical axis 204. In particular, if vertical axis 204 is the vertical axis that the L-shaped robotic arm moves along, vertical axis 202 may be the vertical approach axis for the robotic grip and twist assembly 30. In such embodiment, an end of the L-shaped robotic arm may be fixed to the side of the main housing of the robotic arm grip and twist assembly 30.

Figure 15:
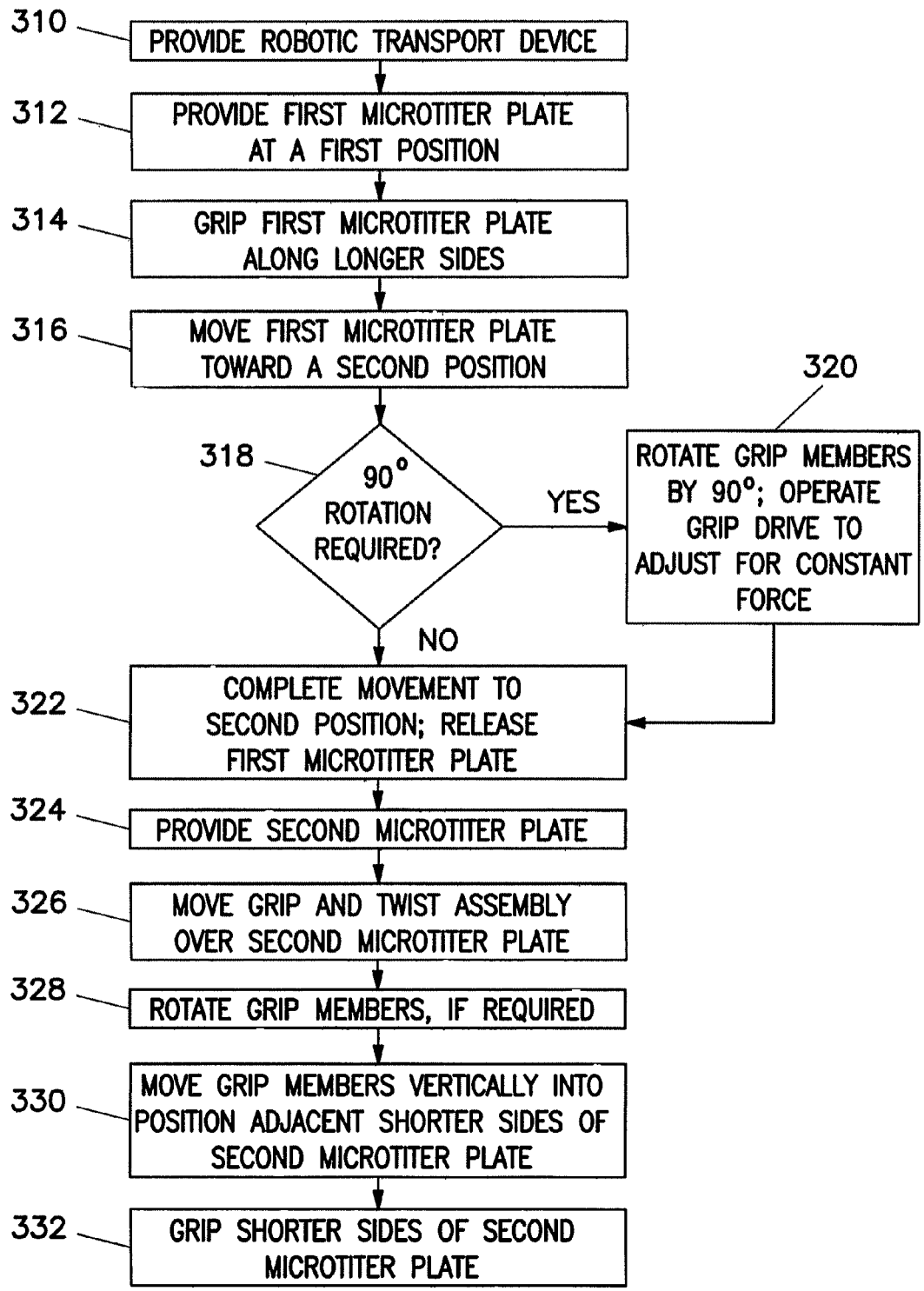
FIG. 15 is a flow chart of a method of transporting microtiter plates in association with the robotic grip and twist assembly of FIG. 2.

Based on the above description, it can be seen that the device described herein is configured to perform a method of liquid handling wherein laboratory microtiter plates are gripped in various orientations and along different sides. An example series of method steps using such a device is shown in FIG. 15. With reference to FIG. 15, the first step 310 of the exemplary method involves providing a robotic transport device as described above. The robotic transport device comprises a robotic arm supporting a first gripping member and a second gripping member opposed to the first gripping member, wherein the first gripping member and second gripping member are rotatable relative to the robotic arm. Next, in step 312, a first microtiter plate is provided at a first location, such as a microtiter plate dispenser. The first microtiter plate includes a plurality of wells, two opposing longer sides and two opposing shorter sides. In step 314, the robotic transport assembly is used to grip the first microtiter plate in a portrait orientation by bringing the first gripping member and the second gripping member into contact with the opposing longer sides of the first microtiter plate.

After gripping the first microtiter plate in step 314, the first microtiter plate is moved to a second location in step 316, such as a liquid dispense location. During this movement, the first gripping member and the second gripping member may be rotated by 90°, if necessary, moving the microtiter plate from a portrait orientation to a landscape orientation in order to properly align the microtiter plate for the second location. Steps 318 and 320 note the possibility for a 90° rotation.

If the grip members 40, 42 and microtiter plate are rotated by 90°, a grip torque correction must be made in step 320. In particular, with reference again to FIG. 3, operation of the twist drive 34 will cause the gripper block 38 to rotate. The gripper block 38 holds the gear racks 60, 62, which engage pinion 54 of the grip drive 32. Rotation of the gripper block 38 will cause the gear racks 60, 62 to move around the pinion 54, and result in movement of the grip members 40, 42. Movement of the grip members 40, 42 is not desired, as such movement may cause too much or too little force to be applied to the sides of the microtiter plate. Thus, when the twist drive 34 is operated to rotate the grip members and microtiter plate, the grip drive 32 is also operated to prevent movement of the grip members 40, 42 relative to one another and thus maintain a constant gripping force provided by the grip members 40, 42 upon the first plate.

With continued reference to FIG. 15, after gripping the first microtiter plate in a portrait orientation along the longer sides of the plate, rotating the plate (if applicable), and moving the plate to the second location, the first microtiter plate is released in step 322. Next, liquid transport device directs its attention to a second microtiter plate provided in step 324 at the second location. Like the first microtiter plate, the second microtiter plate also includes a plurality of wells, two opposing longer sides and two opposing shorter sides. In step 326, the grip members are moved into position to grip the second microtiter plate by moving the grip and twist assembly directly over the second microtiter plate. In step 328, the grip members 40, 42 are then rotated so they are in position to grip the shorter sides of the second microtiter plate. In step 330, the grip members are moved in a vertical direction and positioned adjacent to the opposing shorter sides of the second microtiter plate. Thereafter, in step 332, the grip drive is operated, causing the grip members to contact the opposing shorter sides of the second microtiter plate, thus grasping the second microtiter plate so that it can be moved to another location. Accordingly, the above method shows that the robotic transport device described herein is operable to make a vertical approach to a microtiter plate and grasp the microtiter plate by bringing its grip members into contact with either the opposing shorter sides or opposing longer sides of the microtiter plate.

Although the present invention has been described with respect to certain preferred embodiments, it will be appreciated by those of skill in the art that other implementations and adaptations are possible. For example, the opposing grip members may take on different shapes and sizes and shapes different from those shown. As another example, the drive mechanisms used in the grip drive and the twist drive may be different from those disclosed herein. Of course, numerous other examples exist of implementations and adaptations that are different from the certain preferred embodiments disclosed herein. Moreover, it should be noted that there are advantages to individual advancements described herein that may be obtained without incorporating other aspects described above. Therefore, the spirit and scope of the appended claims should not be limited to the description of the preferred embodiments contained herein.

What is claimed is:

1. A device configured to grip a microtiter plate having a plurality of wells, the microtiter plate comprising two opposing first sides and two opposing second sides wherein the length of each opposing first side is longer than the length of each opposing second side, the device comprising:

a Cartesian coordinate robot configured to move a robotic arm in at least one horizontal and vertical axis, the robotic arm having a central, vertical axis;

a grip and twist assembly connected to an end of the robotic arm, the grip and twist assembly including a grip drive motor, a twist drive motor, a first gripping member and a second gripping member opposed to the first gripping member;

wherein the first gripping member and the second gripping member are coupled t the grip drive motor such that actuation of the grip drive motor causes the first gripping member and the second gripping member to move toward or way from the central, vertical axis of the vertical robotic arm;

wherein the first gripping member and the second griping member are coupled to the twist drive motor such that actuation of the twist drive motor causes the first gripping member and the second gripping member to rotate about a vertical axis of rotation;

and wherein the first gripping member and second gripping member are configured to move relative to each other between a first gripping position and a second gripping position, wherein the first gripping member and the second gripping member are adapted to grip the two opposing first sides of the microtiter plate in the first gripping position, and wherein the first gripping member and the second gripping member are configured to grip the two opposing second sides of the microtiter plate in the second gripping position;

and a microprocessor configured to direct the Cartesian coordinate robot, in response to a command to transfer the microtiter plate from a first location to a second location wherein the second location is associated with one of the first gripping position and the second gripping position, to select one of the first gripping position and the second gripping position based on the second location, to engage the twist drive motor to rotate the first gripping member and the second gripping member to the selected one of the first gripping position and the second gripping position if necessary, to position the robotic arm such that the microtiter plate is between the first gripping member and the second gripping member and to engage the grip drive motor to grasp the microtiter late at the first location in the selected one of the first gripping position and the second gripping position.

2. The device of claim 1 wherein the central, vertical axis of the robotic arm is positioned between the first gripping member and the second gripping member.

3. The device of claim 1 wherein the central, vertical axis of the robotic arm and the vertical axis of rotation of the gripping member are the same axis.

4. The device of claim 1 wherein the first gripping member comprises a first gripping surface, and wherein the second gripping member comprises a second gripping surface.

5. The device of claim 4 wherein the second gripping member further comprises a third gripping surface.

6. The device of claim 1 wherein the Cartesian coordinate robot further comprises a support member having a drive train that moves the robotic arm in the vertical axis.

7. The device of claim 6 wherein the support member is configured to ride on a horizontal track, and wherein the support member is configured to move in a horizontal direction upon the horizontal track.

8. The device of claim 1 wherein the twist drive and the grip drive each comprise a servo-controlled motor.

9. The device of claim 1 wherein the distance between the first gripping member and the second gripping member is about 3 and 3/8 inches in the first position and wherein the distance between the first gripping member and the second gripping member is about 5 inches in the second position.

10. The device of claim 1, wherein the microprocessor is further configured to direct the Cartesian coordinate robot to rotate the grasped microtiter plate based on the second location.

* * * * *